United States Patent [19]
Nelson

[11] Patent Number: 6,022,332
[45] Date of Patent: Feb. 8, 2000

[54] ANKLE BRACE ALLOWING FLEXION AND EXTENSION

[75] Inventor: Ronald E. Nelson, Chetek, Wis.

[73] Assignee: Private Label Creations, Inc., Chetek, Wis.

[21] Appl. No.: 08/873,542

[22] Filed: Jun. 12, 1997

[51] Int. Cl.[7] .............................. A61F 5/00; A61F 13/00
[52] U.S. Cl. .............................. 602/27; 602/65; 128/882
[58] Field of Search ................................ 602/23, 27, 62, 602/65; 128/882

[56] References Cited

U.S. PATENT DOCUMENTS

| | | | |
|---|---|---|---|
| 1,037,441 | 9/1912 | Collis | 601/65 |
| 1,231,332 | 6/1917 | Collis | 602/65 |
| 2,994,322 | 8/1961 | Cullen et al. | 602/27 |
| 4,724,847 | 2/1988 | Nelson | 128/80 |
| 4,727,863 | 3/1988 | Nelson | 128/80 |
| 4,825,856 | 5/1989 | Nelson | 128/80 |
| 5,000,195 | 3/1991 | Neal | 602/27 |
| 5,472,411 | 12/1995 | Montag et al. | 128/882 X |

*Primary Examiner*—Richard J. Apley
*Assistant Examiner*—Denise Pothier
*Attorney, Agent, or Firm*—Nawrocki, Rooney & Sivertson, P.A.

[57] ABSTRACT

An ankle brace designed to limit inversion, eversion and twisting movements while allowing near-normal flexion and extension. The ankle brace includes a medial member and a lateral member, each of which has a forward edge, a bottom edge and a rearward edge. The forward edges are associated with one another to define a front support portion of the ankle brace. Similarly, the bottom edges are connected and define a base support portion of the ankle brace. Finally, the rearward edges are associated with one another to define a rear support portion which further includes a one direction stretch material strip. The material strip is disposed at the rear support portion such that during use, the material strip stretches with flexion of the user's ankle. However, the material strip and remaining components remain relatively rigid in other directions to limit inversion, eversion and twisting movements.

16 Claims, 6 Drawing Sheets

ANKLE BRACE ALLOWING FLEXION AND EXTENSION

BACKGROUND OF THE INVENTION

The present invention relates to an improved ankle brace. More particularly, it relates to an ankle brace including single direction stretch material along a rear portion to facilitate near-normal flexion and extension movements while limiting inversion, eversion and rotational movements.

The human ankle joint is a unique anatomical structure. The ankle includes seven bones, referred to as tarsal bones, one of which is a talus or ankle bone. The talus bone forms a lower half of an ankle joint. The upper half of the ankle joint is formed by tibia and fibula bones of the lower leg. The lower portion of the tibia forms a medial malleolus or inner portion of the ankle. The lower portion of the fibula forms a lateral malleolus or outer portion of the ankle. The fibula and tibia are held together by ligaments and form a mortice to receive the talus.

A relatively complex ligament system holds the ankle joint together. The ankle, or tibiofibular, joint includes three separate articulations; the inferior tibiofibular joint which is the articulation between the lateral malleolus and the tibia, the tibiofibular union which is the union of the shafts of the tibia and fibula by an interosseous membrane that consists of numerous short fibers which pass transversely from one articular surface to the other, and a superior tibiofibular articulation which is an articulation between the head of the fibula and a fibular facet of the tibia. During flexion in which the foot is pivoted toward the leg, the fibula tends to be displaced upward. Conversely, an extension movement, or pivoting of the foot away from the leg, the fibula tends to be displaced downward. These movements are normally resisted by the interosseous membrane. However, normal walking movements involve the simple flexion and extension of the foot relative to the leg.

While the human ankle is constructed to be highly durable, injuries can and do happen. Oftentimes during strenuous activities or sports participation, the foot is forced into an inversion or eversion position. Inversion is movement of the foot inward with respect to the leg. Conversely, eversion is a sideways, outward movement of the foot with respect to the leg. While the ankle joint structure does allow for minor natural inversion or eversion, overexertion in either of these directions results in stretching of the ankle joint, more commonly referred to as an "ankle sprain". For example, a common basketball or volleyball-related injury occurs when a participant lands on a side of the foot, causing the ankle to "roll" in an inverted or everted fashion. Alternatively and even more problematic is a bone fracture of one of the ankle bones. For example, a common skiing-related injury occurs when the foot is severely twisted with respect to the leg, fracturing the lateral or medial malleoli.

Immobilization of the ankle joint is commonly required to facilitate requisite healing following injury. Obviously, when a bone fracture has occurred, an immobilizing cast is required. However, for less severe injuries, the ankle need only be immobilized so as to restrict inversion, eversion and twisting movements. In other words, where the injury is such that the person may still engage in flexion and extension movements, such as normal walking or running, the ankle need only be partially immobilized. Normal flexion-extension of the foot will not magnify or otherwise aggravate the injury.

One common method for partially immobilizing an ankle is wrapping athletic tape around the person's foot, ankle and lower leg. To provide additional support, the user's ankle and lower leg is taped to the user's shoe. While the athletic taping approach is widely accepted, it does not provide support for an adequate period of time. Once applied, repeated movement of the foot causes the tape to loosen. Thus, after as little as 15 minutes of activity, the tape no longer provides the necessary inversion, eversion and twisting support required to prevent injury. Further, while a single roll of athletic tape is inexpensive, constantly retaping the injured area will, over time, require a relatively significant expenditure.

In view of the above-described problems associated with taping an injured ankle, various reusable ankle braces have been developed. Generally speaking, the standard ankle brace is designed to mimic the effects of the taping approach, but for a longer period of time and at a reduced cost. The standard ankle brace is basically a boot-shaped structure defined by a lateral member and a medial member. The lateral and medial members are configured to approximately match the contours of the lateral and medial members of the ankle, respectively. While flexible, the members are made from a non-stretch material. The members define an upper or calf opening for receiving and fitting about the user's calf and dorsal opening for receiving and fitting about the dorsal portion of the user's foot. Thus, the user's toes normally extend from the boot. With this configuration, the boot can accommodate a wide variety of different width feet. Further, the boot normally includes a slit or opening at the heel to facilitate positioning the foot/ankle brace into an athletic shoe. Finally, a front closure device, such as a shoelace, is used to tightly secure the ankle brace about the user's foot.

Unlike athletic tape, the above-described ankle brace does not normally lose its resiliency over time. Therefore, the ankle brace can provide the long-term support not otherwise found with athletic tape. Unfortunately, however, the standard ankle brace design has several drawbacks.

Unlike a permanent cast, the purpose of taping or use of an ankle brace is to partially immobilize the ankle joint. Once again, most ankle-related injuries, such as an ankle sprain, are not further traumatized by flexion and/or extension movements. The standard ankle brace design, however, does not allow for this type of movement. Instead, the standard ankle brace limits all movements. Thus, a person wearing a standard ankle brace is unduly restricted from performing normal range walking or running movements that require flexion and extension. Where the ankle brace is worn as a precautionary measure, the user's performance again will be unnecessarily hindered as he or she is prevented from making normal movements. Further, because the ankle brace is essentially clamped over the user's Achilles tendon, tendinitis may result.

SUMMARY OF THE INVENTION

The present invention provides an ankle brace configured to promote flexion and extension movements while limiting inversion, eversion and twisting. The ankle brace includes a medial member and a lateral member, both of which include a forward edge, a rearward edge and a bottom edge. The medial member and the lateral member are configured to support a human foot and ankle. In this regard, the forward edges of the medial and lateral members are selectively associated to define a front support portion. Further, the bottom edges of the medial and lateral members are attached to define a base support portion. Finally, the rearward edge of the medial member is associated with the rearward edge of the lateral member to define a rear support portion. The rear support portion further includes a strip of single direction stretch material which connects the rearward edges. The material strip is preferably configured to stretch only in a vertical direction.

During use, the ankle brace of the present invention is placed over a user's foot. In the preferred embodiment, the ankle brace includes a calf opening and a tarsal opening for facilitating proper placement of the ankle brace on the foot. Once in place, the ankle brace supports the user's ankle. The base support portion is positioned at a bottom of the foot. The front support portion extends along a superior surface of the foot to a lower portion of the leg or shin. Notably, the front support portion may include tightening means, such as various eyelets disposed along the forward edges of the medial and lateral members in conjunction with a shoelace, by which the user may tighten the ankle brace about the foot and ankle. Finally, the rear support portion extends along the heel and Achilles tendon to a lower portion of the user's calf. The single direction stretch material strip is preferably disposed at a point above the heel.

Once the ankle brace is secure, the user is able to engage in normal activities, such as walking or running. The ankle brace of the present invention fully supports the user's foot and ankle during these activities. The rear support portion in conjunction with other components of the ankle brace limits inversion, eversion and twisting movements, but allows near-normal flexion. More particularly, when the user's foot is flexed toward the leg, the single direction stretch strip stretches vertically. However, the single direction stretch strip is inelastic in a horizontal direction such that inversion, eversion and twisting movements are limited.

DETAILED DESCRIPTION OF THE INVENTION

Figure 1:
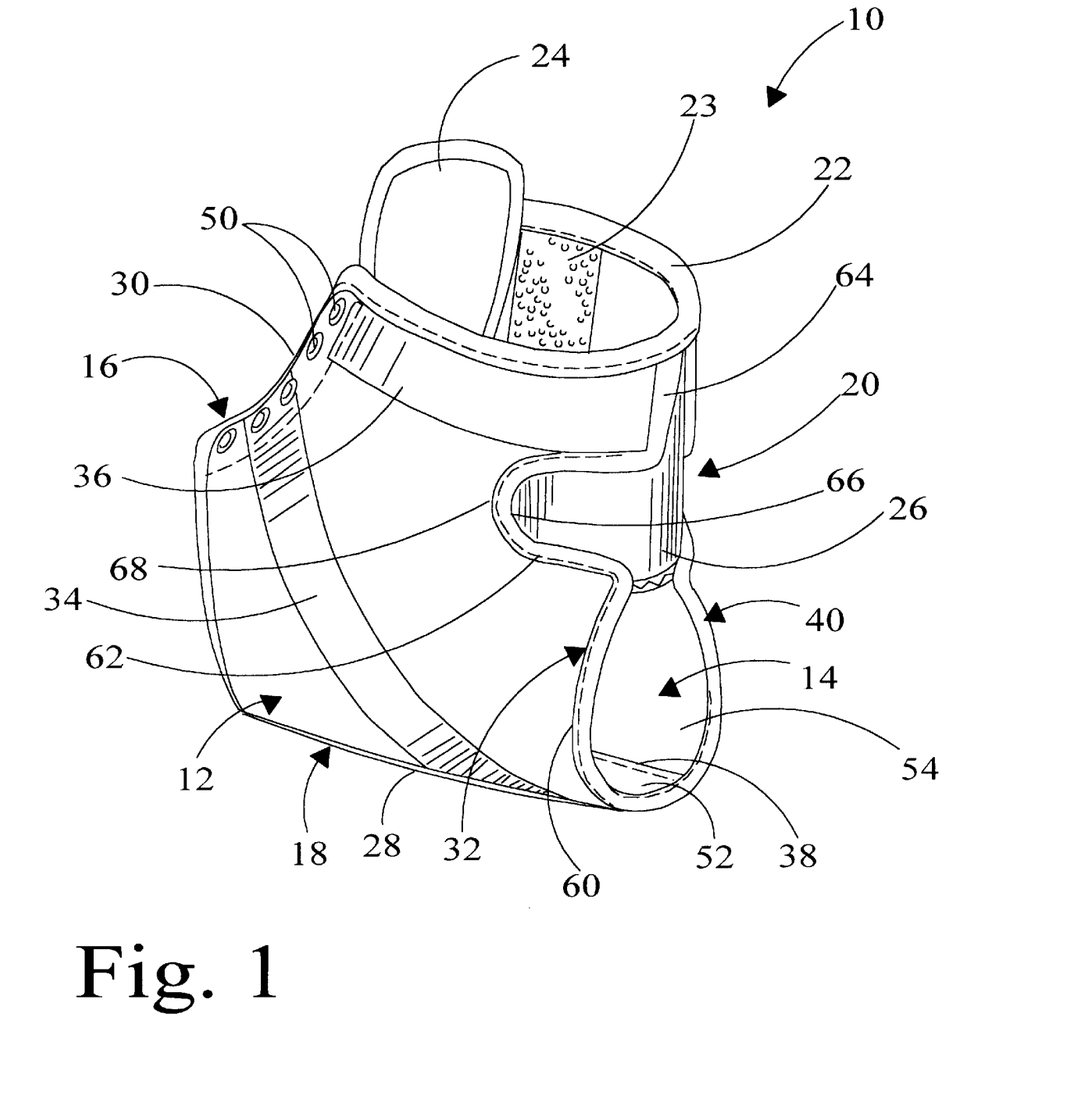
FIG. 1 is a rear perspective view of an ankle brace in accordance with the present invention with a lace removed.

A preferred embodiment of an ankle brace 10 is shown in FIG. 1. The ankle brace 10 includes a medial member 12, a lateral member 14, a front support portion 16, a base support portion 18, a rear support portion 20 and a top edge 22.

The medial member 12 and the lateral member 14 extend from the base support portion 18 and are connected at the front support portion 16 and the rear support portion 20. In this regard, the medial member 12 and the lateral member 14 define a metatarsal opening (not shown) between the base support portion 18 and the front support portion 16. The top edge 22 attaches the medial member 12 and the lateral member 14 and defines a leg opening 23. The front support portion 16 includes a tongue 24. The rear support portion 20 includes a material strip 26.

The medial member 12 is generally configured to encompass a medial malleolus of a user's foot and extends to a lower portion (or tibia) of a user's leg. Thus, the medial member 12 is generally L-shaped. The medial member 12 includes a bottom edge 28, a forward edge 30, a rearward edge 32, a first reinforcement 34 and a second reinforcement 36. The medial member 12 is made of durable, flexible sheet-like material such as canvas having a soft side to be orientated toward the foot. In the preferred embodiment, the medial member 12 is made of a material which will not stretch vertically. The first reinforcement 34 is preferably a strip of relatively rigid material sewn into the medial member 12, orientated to further support a user's arch and dorsal region. Similarly, the second reinforcement 36 is a strip of relatively rigid material sewn to the medial member 12 to provide additional support to a user's lower leg.

The lateral member 14 is configured to support and reinforce a lateral malleolus of a user's ankle and adjacent lower leg portion (or fibula). Although not fully shown in FIG. 1, the lateral member 14 is nearly identical to the medial member 12. Thus, the lateral member 14 includes a bottom edge 38 (shown partially in FIG. 1), a forward edge (not shown), a rearward edge 40, and first and second reinforcements (not shown). The lateral member 14 is made of durable, flexible sheet-like material, such as canvas, having a soft side to be orientated toward a user's foot.

The medial member 12 and the lateral member 14 are preferably sized to extend from a base of a user's foot to the user's calf, and thus have a length of about 9 inches. In the preferred embodiment, the medial member 12 is approximately 0.25 inches shorter in vertical height (before placement over a foot) than the lateral member 14 to conform to an arch of the foot. For example, the medial member 12 is cut at a vertical length of 9 inches and the lateral member 14 is cut at a vertical length of 9.25 inches. With this preferred configuration, by allowing the ankle brace 10 to conform to the arch of the foot, overall support is improved. It should be understood that the medial member 12 and the lateral member 14 may be sized at a variety of identical or varying lengths.

The front support portion 16 is defined by the forward edge 30 of the medial member 12, the forward edge (not shown) of the lateral member 14 and the tongue 24. The front support portion 16 is preferably adapted to encompass a front portion of a human foot (not shown). In the preferred embodiment, the tongue 24 is connected by stitching to the medial member 12 and the lateral member 14 so as to associate the respective forward edges 30. In this regard, the respective forward edges 30 are intermediately curved as shown in FIG. 1 to correspond with a transition region between a user's leg and foot. The front support portion 16 further includes eyelets 50 and a lace (not shown). The eyelets 50 are disposed in opposing relationship on both the forward edge 30 of the medial member 12 and the forward edge (not shown) of the lateral member 14. Similar to a standard shoe, the lace is fed through the eyelets 50, providing the user with means to pull the medial member 12 toward the lateral member 14, thus tightening the ankle brace 10. Alternatively, eyelets 50 may be eliminated with the medial member 12 and lateral member 14 joined at the front support portion 16 by elastic material.

The base support portion 18 is defined by the bottom edge 28 of the medial member 12 and the bottom edge 38 of the lateral member 14. The base support 18 is preferably adapted to underlie a human foot (not shown). In the preferred embodiment, the base support portion 18 includes a support strip 52 connecting the bottom edges 28, 38 of the medial and lateral members 12, 14. The support strip 52 is made of relatively rigid, durable material, and reinforces the ankle brace 10 against wear. The support strip 52 is preferably sewn to the medial and lateral members 12, 14.

The rear support portion 20 is preferably adapted to overlie a human foot and is defined in part by the rearward edge 32 of the medial member 12 and the rearward edge 40 of the lateral member 14. The rear support portion 20 further includes the material strip 26 which connects the rearward edges 32, 40. In this regard, the material strip 26 is disposed near the top edge 22 of the ankle brace 10 and extends to a point slightly above a user's heel. Thus, the rearward edges 32, 40 and the material strip 26 define a heel opening 54 preferably sized to receive a user's heel.

The material strip 26 is made of single direction stretch material. Thus, the material strip 26 is configured to stretch only in a vertical direction, with reference to the orientation shown in FIG. 1. The material strip 26 preferably does not stretch horizontally under normal stress. It should be recognized that depending upon composition of the material strip 26, some limited horizontal stretch may occur. The single directional stretch attribute of the material strip 26 is preferably achieved via an elastomeric material. However, other materials can be used, such as woven or knitted cloth, configured to allow only vertical stretch.

The rearward edges 32, 40 of the medial member 12 and the lateral member 14, respectively, are preferably configured to facilitate vertical stretch of the material strip 26. In this regard, the rearward edges 32, 40 are preferably constructed identically. Therefore, in the interest of brevity, only the rearward edge 32 of the medial member 12 will be described in detail below. It is to be understood, however, that the rearward edge 40 of the lateral member 14 is similarly constructed.

The rearward edge 32 of the medial member 12 includes a lower segment 60, an intermediate segment 62 and an upper segment 64. The lower segment 60 extends from the bottom edge 28 in a relatively linear fashion. The intermediate segment 62 is preferably arc-shaped, defining a window or movable slot 66. In other words, the intermediate segment 62 extends toward the forward edge 30 to an apex 68. The intermediate segment 62 then extends from the apex 68 away from the forward edge 30. Finally, the upper segment 64 extends in a relatively linear fashion from the intermediate segment 62 to the top edge 22.

The arc-shaped intermediate segment 62 facilitates vertical stretch of the material strip 26. As described in greater detail below, when the base support portion 18 is forced away from the top edge 22, the lower segment 60 is pulled away from the upper segment 64 via extension of the intermediate segment 62. Basically, the rearward edge 32 "pivots" at the apex 68 of the intermediate segment 62. Further, as the lower segment 60 moves away from the upper segment 64, the material strip 26 is stretched vertically.

While the intermediate segment 62 has been preferably described as being arc-shaped, other configurations are equally acceptable. Importantly, the intermediate segment 62 only partially extends toward the forward edge 30. In other words, the window 66 created by the intermediate segment 62 cannot extend so as to encompass the medial malleolus, as with such a configuration, eversion movements would not be limited.

Figure 2:
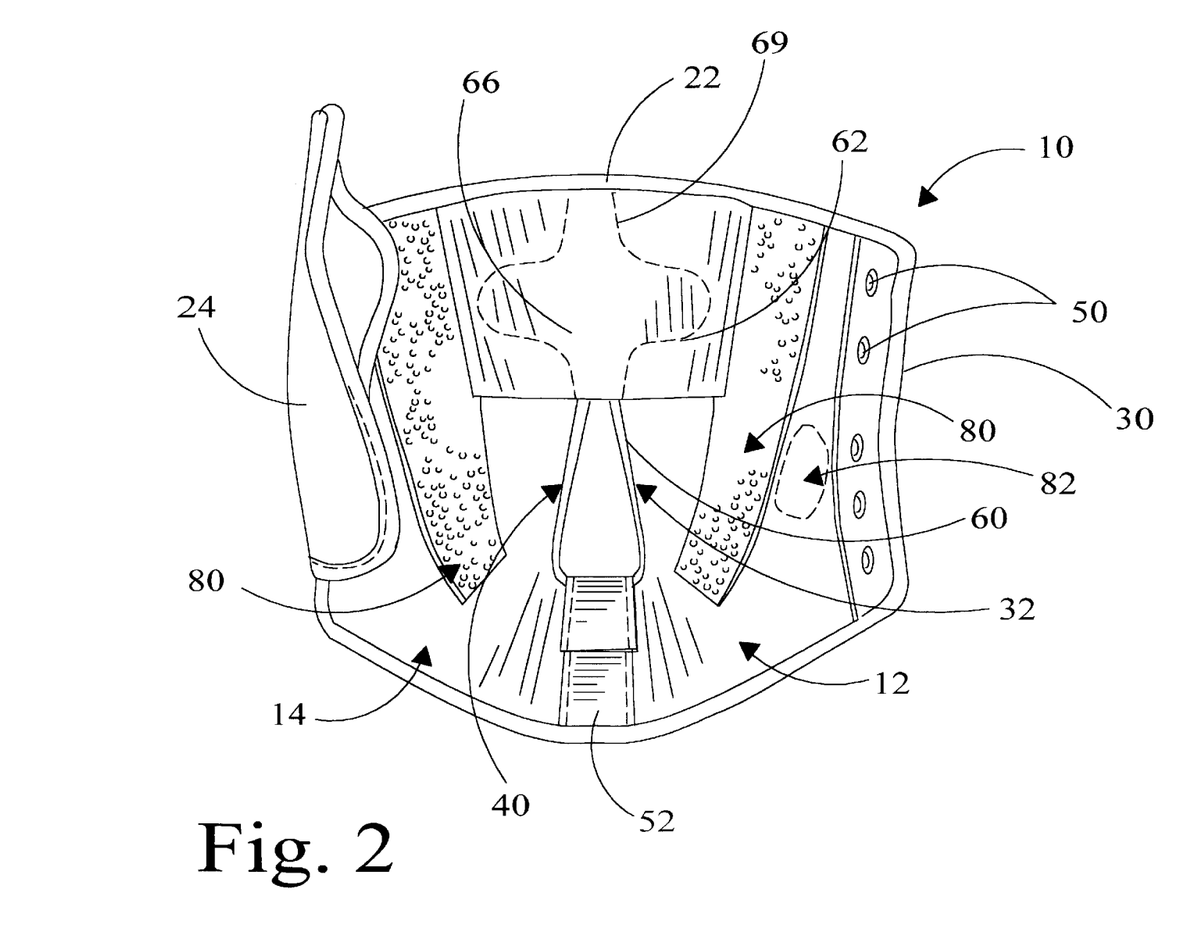
FIG. 2 is a front plan view of the ankle brace of the present invention with lace removed and in a spread open configuration to show the inside thereof.

As shown in FIG. 2, the rearward edge 40 of the lateral member 14 is preferably constructed identically to the rearward edge 32 of the medial member 12. The material strip 26 is preferably sewn to the rearward edges 32, 40 at an interior of the ankle brace 10. Further, the material strip 26 is attached by stitching to the top edge 22 of the ankle brace 10. In the preferred embodiment, the material strip 26 has a length of 3.5 inches and a width sufficient to encompass the window 66 created by the rearward edges 32, 40. Thus, in the preferred embodiment, the material strip 26 has a width of 1.5 inches. It should be understood, however, that other dimensions are equally acceptable so long as the material strip 26 is large enough to allow near-normal flexion movements.

Finally, as shown in FIG. 2, the preferred ankle brace 10 includes stirrup retaining means 80 for engaging an extension stirrup (described in greater detail below) and a recessed area, shown generally at 82. The stirrup retaining means 80 are preferably disposed in an opposing relationship along an interior of the medial member 12 and the lateral member 14. In the preferred embodiment, the stirrup retaining means 80 are in the form of loop-like filaments of the type commonly sold under the trademark VELCRO®.

Figure 3:
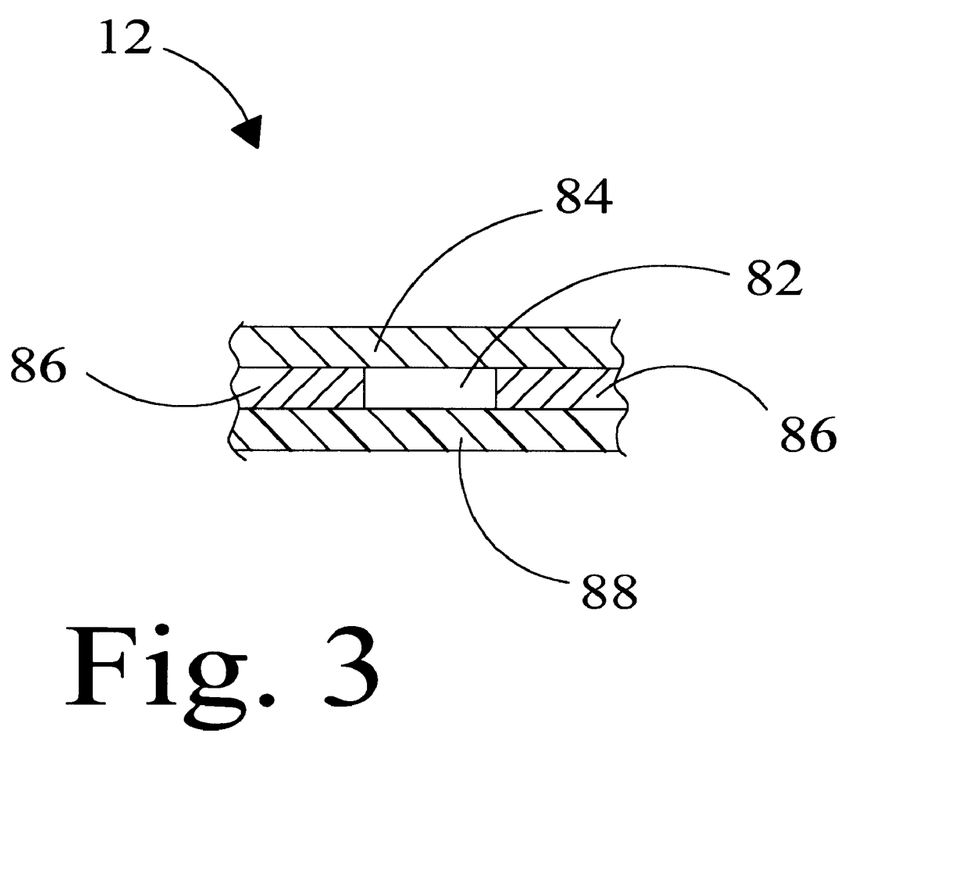
FIG. 3 is an enlarged, cross-sectional view of a recessed area of the ankle brace in accordance with the present invention.

Greater details on the recessed area 82 are provided in FIG. 3, which is an enlarged cross-sectional view of a portion of the medial member 12. As shown in FIG. 3, the medial member is comprised of an outer layer 84, an intermediate layer 86 and an inner layer 88. In a preferred embodiment, the outer layer 84 is made of a relatively strong fabric, such as ANSOTEX®, configured to resist wear while providing ankle stability to a user. The intermediate portion 86 is preferably a coarse fabric, such as vinyl. Finally, the inner layer 88 is a cloth-like material. Because the inner layer 88 is in direct contact with a user's foot, the inner layer is soft to minimize skin irritation, but will preferably absorb sweat.

As shown in FIG. 3, the recessed area 82 is formed in the intermediate layer 86. In one preferred embodiment, the recessed area 82 is formed by a die cut during manufacture of the medial member 12. Thus, the recessed area 82 is a layer of material removed from the medial member 12 to minimize pressure on an ankle bone (not shown) during use. The lateral member 14 may also include a recessed area. Alternatively, the ankle brace 10 need not include the recessed area 82.

With reference to FIGS. 1 and 2, a user's foot (not shown) is simply slid into engagement with the ankle brace 10. The ankle brace 10 has been described for placement over a user's right foot. It should be understood, however, that the ankle brace 10 for placement over a user's left foot is identically configured. When properly positioned, the metatarsals and phalanges portions of the user's foot extend forwardly from the front support portion; the heel extends through the heel opening 54; and the lower leg extends from the leg opening 23. The medial member 12 supports a medial malleolus bone, whereas the lateral member 14 supports a lateral malleolus bone. The front support portion 16 rests along a superior front portion of the user's foot. The base support portion 18 underlies a foot base and arch. Finally, the rear support portion 20 overlies the user's Achilles tendon. The ankle brace 10 is secured in this position by tightening the lace (not shown) relative to the eyelets 50 so that the top edge 22 is snug about the user's lower leg.

During use, the ankle brace 10 limits inversion and eversion of the user's foot. The medial and lateral members 12, 14 will not stretch vertically. Therefore, the medial and lateral members 12, 14 prevent eversion and inversion respectively. Further, as previously described, the material strip 26 does not stretch horizontally. Therefore, the ankle brace 10 also limits horizontal twisting of the ankle. However, flexion and extension movements are allowed.

More particularly, a flexion movement pulls the lower segment 60 of the rearward edges 32, 40 away from the upper segment 64. The vertical stretch characteristic of the material strip 26 allows this movement to occur. In other words, the lower segment 60 and the upper segment 64 are attached to the material strip 26. As the lower segment 60 pulls away from the upper segment 64, the material strip 26 stretches vertically. The intermediate segment 62 of the rearward edges 32, 40 extends slightly in conjunction with this vertical stretch of the material strip 26. When the foot returns to a normal position, the material strip 26 is resilient so as to return the rear support portion 20 to the position shown in FIG. 1.

Conversely, when the foot is extended, the material strip 26 has sufficient flexibility to collapse on itself. Thus, with an extension movement, the lower segment 60 of the rearward edges 32, 40 move toward the upper segment 64. The material strip 26 collapses with this movement, as does the intermediate segment 62. Thus, the rear support portion 20 is configured to allow near-normal extension and flexion movements. A user can engage in normal walking or running motions without undue restriction.

Figure 4:
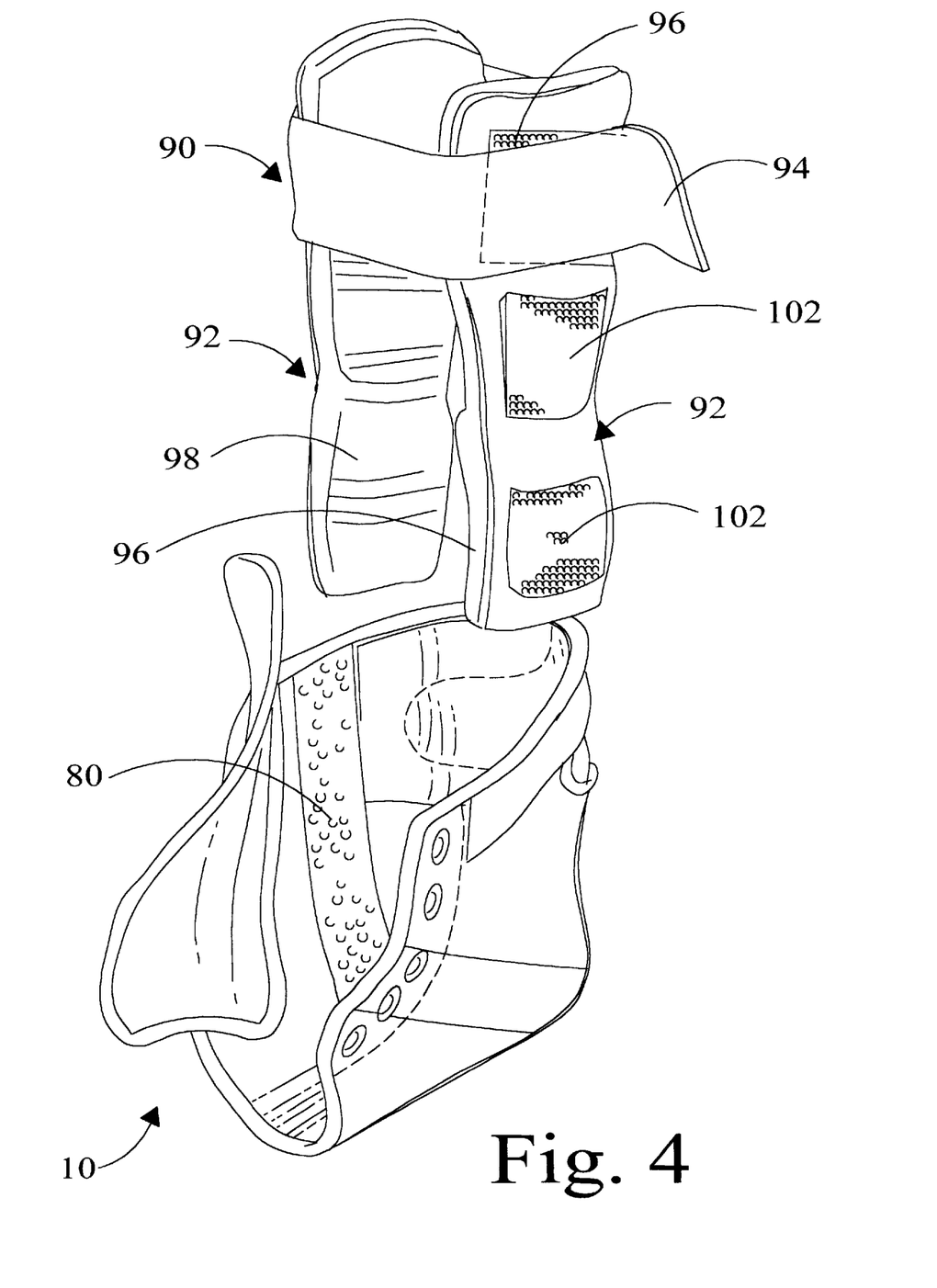
FIG. 4 is an exploded, perspective view of the ankle brace of FIG. 1 and a support stirrup.

As previously described, the ankle brace 10 is preferably designed to selectively receive an extension stirrup 90, as shown in FIG. 4. The extension stirrup 90 is configured to provide additional support along a user's leg, and includes opposing legs 92, a strap 94 and strap retaining means 96. Each of the opposing legs 92 includes a foam interior 98, a reinforced exterior 98, brace retention means 102 and strap retaining means 96. The foam interior 96 is configured to conform with a human foot, ankle and lower leg. Further, the foam interior 98 is preferably made of a soft material so that the extension stirrup 90 may be worn comfortably. The reinforced exterior 100 generally conforms in shape to that of the foam interior 98. Further, the reinforced exterior 98 is preferably made of a rigid material, such as hardened plastic. The brace retaining means 102 are configured to mate with the stirrup retaining means 80 disposed within the ankle brace 10. Thus in the preferred embodiment, the brace retaining means 102 are strips which form a corresponding releasable closure means in the form of hook-like filaments of the type commonly sold under the trademark VELCRO®. Finally, the strap retaining means 96 is preferably configured to selectively secure a portion of the retention strap 94. In this regard, the strap retaining means 96 is a material strip in the form of loop-like filaments of the type commonly sold under the trademark VELCRO®.

The strap 94 connects the opposing legs 92. The strap 94 is preferably made of a flexible, yet inelastic material such as canvas, and is permanently attached at one end to one of the opposing legs 92. Further, the retention strap 94 includes a retaining means (not shown) which selectively mates with the strap retaining means 96 otherwise disposed on one of the opposing legs 92.

The extension stirrup 90 is secured to the user's foot (not shown) and lower leg prior placement of to the ankle brace 10. More particularly, the opposing legs 92 are positioned on opposite sides of the user's leg such that the opposing legs 92 extend to a base portion of the user's foot. The strap 94 is wrapped around the opposing legs 92 as shown and secured to the strap retaining means 96, securing the extension stirrup 90 to the user's leg. Once in place, the user's foot is then positioned within the ankle brace 10 as previously described. The brace retaining means 102 of the opposing legs 92 are secured to the stirrup retaining means 80 within the ankle brace 10. When properly positioned, the extension stirrup 90 serves to further limit inversion and eversion movements.

Figure 5:
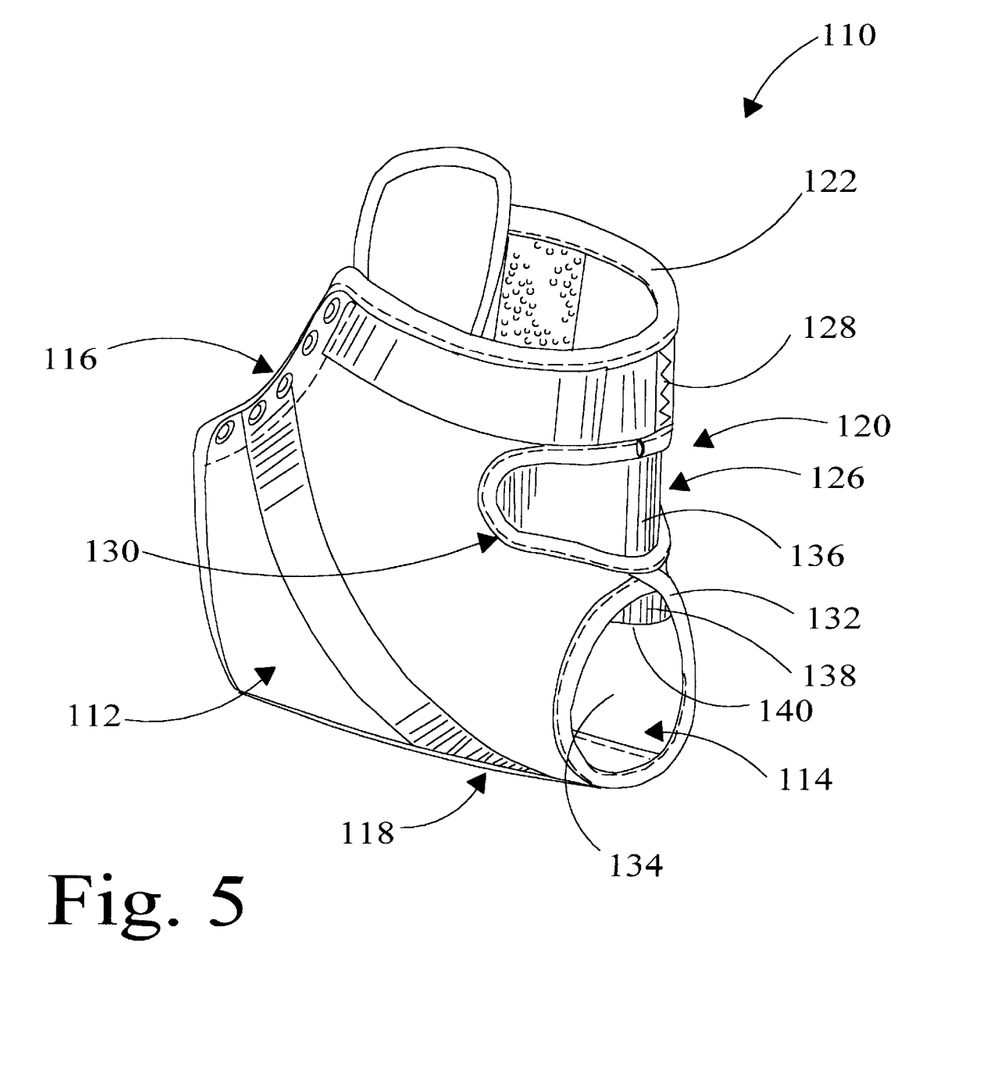
FIG. 5 is a rear perspective view of an alternative ankle brace in accordance with the present invention.

An alternative embodiment of an ankle brace 110 is shown in FIG. 5. The ankle brace 110 shown in FIG. 4 is highly similar to the ankle brace 10 of FIGS. 1 and 2. Thus, the ankle brace 110 includes a medial member 112, a lateral member 114, a front support portion 116, a base support portion 118, a rear support portion 120 and a top edge 122. The medial 112, lateral 114, front support 116 and base support 118 portions and the top edge 122 are identical to those shown in FIGS. 1 and 2.

The rear support portion 120, however, includes a material strip 126, an upper closure 128, a window 130, a lower closure 132 and a heel opening 134. The material strip 126 is disposed at an interior of the ankle brace 110 and encompasses the window 130. The upper closure 128 defines a top portion of the window 130 and connects the medial member 112 and the lateral member 114.

The window 130 is positioned slightly below the top edge 122 of the ankle brace 110 and is defined by the medial member 112, the lateral member 114, the upper closure 128 and the lower closure 132. In this regard, the window 130 extends from the rear support portion 120 toward the front support portion 116. In the preferred embodiment, the window 130 is reinforced with additional stitching. The lower closure 132 is attached to a portion of the material strip 126 and connects the medial member 112 and the lateral member 114. The lower closure 132 is preferably positioned at a point above the user's heel. Finally, the heel opening 134 is sized to receive a user's heel.

The material strip 126 includes an Achilles portion 136 and a heel portion 138. The Achilles portion 136 is sized to encompass the window 130. The heel portion 138 is sized to extend from the lower closure 132 into the heel opening 134.

Similar to the material strip 26 of FIGS. 1 and 2, the Achilles portion 136 of the material strip 126 shown in FIG. 4 is preferably comprised of a single direction stretch material, such as woven elastic or knitted cloth. Regardless of composition, the Achilles portion 136 is designed to stretch vertically, while remaining rigid in a horizontal orientation. Similarly, the heel portion 138 is designed to have a one-directional stretch attribute. However, the heel portion 138 stretches horizontally. Finally, a bottom 140 of the heel portion 138 is "open" or unsupported so that horizontal stretch is not impeded.

In the preferred embodiment, the Achilles portion 136 has a length of 3.5 inches whereas the heel portion 138 has a length of 1 inch. The Achilles portion 136 is attached to the heel portion 138 with a zig-zag stitch. The Achilles portion 136 is sized to conform with an Achilles tendon of a user's foot. The heel portion 138 is sized to conform with a user's heel. Thus, the Achilles portion 136 and the heel portion 138 work in concert to control heel and ankle movement.

The ankle brace 110 of FIG. 5 functions similar to the ankle brace 10 of FIGS. 1 and 2. The ankle brace 110 is placed over a user's foot and lower leg as previously described. The medial member 112 is made of a vertically inelastic material so as to limit inversion. Similarly, the lateral member 114 is vertically inelastic to limit eversion. The rear support portion 120 limits twisting but allows flexion and extension movements. With a flexion movement, the lower closure 132 is pulled away from the upper closure 128. The Achilles portion 136 of the material strip 126 stretches vertically. The window 130 allows the material strip 126 to stretch, elongating in the vertical direction. The Achilles portion 136 of the material strip 126 has a resiliency to return the rear support portion 120 to the position shown in FIG. 4 when the flexion movement is ceased.

The heel portion 138 of the material strip 126 allows both vertical and horizontal movements. The heel portion 138 conforms to a top portion of the user's heel so as to maintain the user's foot within the ankle brace 110.

Figure 6:
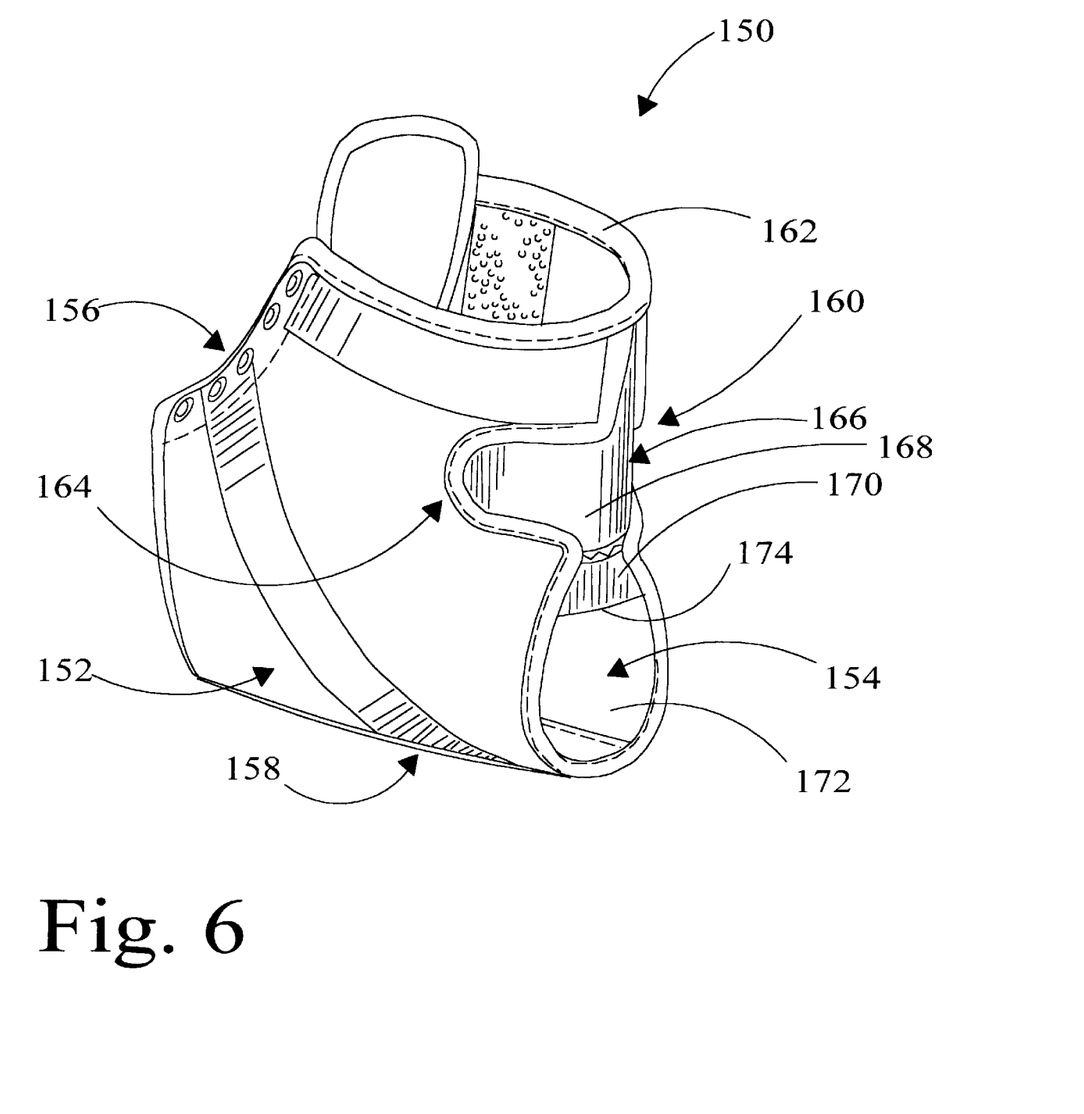
FIG. 6 is a rear perspective view of another alternative ankle brace in accordance with the present invention.

Another alternative embodiment of an ankle brace 150 in accordance with the present invention is shown in FIG. 6, which is highly similar to the ankle brace 10 of FIGS. 1 and 2. Thus, the ankle brace 150 includes a medial member 152, a lateral member 154, a front support portion 156, a base support portion 158, a rear support portion 160 and a top edge 162. The rear support portion 160 includes a window 164 and a material strip 166 having an Achilles portion 168 and a heel portion 170. The Achilles portion 168 is sized to encompass the window 164. The heel portion 170 is attached to the Achilles portion 168 with a zig-zag stitch and extends into a heel opening 172.

The Achilles portion 168 is preferably comprised of a single stretch material, such as woven elastic or knitted cloth, designed to stretch vertically, while remaining relatively rigid horizontally. The heel portion 170 is configured to stretch horizontally, and includes an open end 174.

The ankle brace 150 of FIG. 6 functions similar to the ankle brace 10 of FIGS. 1 and 2, and the ankle brace 110 of FIG. 5. Basically, once placed over a user's foot (not shown), the ankle brace 150 limits inversion, eversion and twisting while allowing near-normal flexion and extension. The Achilles portion 168 and heel portion 170 stretch vertically to allow flexion. Because the Achilles portion 168 is relatively rigid horizontally, twisting motions are impeded. Finally, the horizontal stretch attribute of the heel portion 170 conforms to a user's heel to maintain the ankle brace 150 about the foot.

The ankle brace of the present invention overcomes the problems associated with prior art ankle braces. The ankle brace limits inversion, eversion and twisting movements. However, by utilizing a single direction stretch material strip at the rear support portion, the ankle brace allows near-normal flexion and extension movements. Thus, a user is not unduly restricted when walking and/or running. Further, the rear support portion of the present invention eliminates much of the stress and pressure on the Achilles tendon found with the standard ankle brace design. The ankle brace of the present invention is not clamped down on the Achilles tendon. Therefore, the ankle brace will not cause tendinitis. Importantly, the vertical stretch material of the present invention is not limited to ankle brace application. In other words, recognition of the benefits achieved with a placement of vertical stretch material in the heel area can be applied to other foot-related art. For example, a standard "high top" athletic shoe can be modified to include a strip of vertical stretch-only material in the heel area of the shoe. With is configuration, the athletic shoe acts as a form of an ankle brace, allowing near normal flexion and extension movements, while limited damaging inversion and eversion.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims. For example, the preferred embodiment has been described as including an extension stirrup and means within the ankle brace for retaining the extension stirrup. However, the extension stirrup is only an additional accessory that can be used with the ankle brace of the present invention. Therefore, the extension stirrup is in no way a required element.

Similarly, the ankle brace has been described as having separable medial and lateral members. However, the ankle brace can be manufactured as a single piece of material which defines the medial and lateral members. Additionally, the reinforcements disposed on the medial and lateral members are not required. Finally, the general design of the ankle brace is only one example of an acceptable approach. A wide variety of other designs can be utilized, so long as the rear support portion having a single direction stretch material located above the heel is included.

What is claimed is:

1. An ankle brace to be worn on a human foot and ankle comprising:

a medial member having a forward edge, a bottom edge and a rearward edge;

a lateral member having a forward edge, a bottom edge and a rearward edge;

a front support adapted to encompass a front portion of a human foot, the front support associating the forward edges of the medial member and the lateral member;

a base support portion adapted to underlie a bottom of a human foot, the bottom edges of the medial member and the lateral member being attached to define the base support portion; and a rear support portion adapted to overlie an Achilles tendon of a human foot, the rear support portion including a material strip attached to the rearward edges of the medial member and the lateral member, the material strip having a one direction stretch material oriented to stretch in a vertical but not a horizontal direction such that the rear support portion allows flexion movement of the foot while limiting inversion, eversion and twisting movements of the foot.

2. The ankle brace of claim 1, wherein the rear support portion further includes a window formed by the rearward edges of the medial member and the lateral member for allowing flexion movement.

3. The ankle brace of claim 2, wherein the window is positioned above a heel receiving area of the rear support portion.

4. The ankle brace of claim 2, wherein the material strip encompasses the window.

5. The ankle brace of claim 2, wherein the rearward edges of the medial and lateral members each include a lower segment, an intermediate segment and an upper segment, the window being defined by the intermediate segments of the medial and lateral members, each of which are configured to allow the lower segment to move away from the upper segment in response to flexion movement.

6. The ankle brace of claim 5, wherein the intermediate segments of the medial and lateral members are configured to allow the lower segment to move towards the upper segment in response to an extension movement.

7. The ankle brace of claim 5 wherein the intermediate segments are arc-shaped having an apex distal the front support portion such that the intermediate segment forms a recessed area for allowing flexion movement.

8. The ankle brace of claim 1, wherein the material strip includes an Achilles portion and a heel portion, the Achilles portion being configured to have a one direction stretch characteristic and the heel portion is configured to have a two direction stretch characteristic.

9. The ankle brace of claim 1, wherein the material strip is made of a woven material.

10. The ankle brace of claim 1, wherein the medial member and the lateral members define an interior and exterior, the material strip being disposed at the interior of the medial member and the lateral members.

11. The ankle brace of claim 1, further including:

an extension stirrup configured for selective attachment within the medial member and the lateral member for further supporting a human foot.

12. An improved ankle brace for supporting a human ankle, the ankle brace including a base configured to conform and encompass the ankle and proximal foot on forward, rearward, medial and lateral sides thereof, the base including a lateral member and a medial member, the lateral member and medial member being connected at a bottom portion, a front portion and a rear portion, the improvement comprising:

a strip having one directional stretch material connecting the rear portions of the lateral member and the medial member, the material strip being oriented to stretch in a vertical but not a horizontal direction to allow flexion of the ankle while inhibiting twisting.

13. The improved ankle brace of claim 12, wherein the rear portion of the medial member and the rear portion of the lateral member define a recessed area, the material strip being disposed across the recessed area.

14. The improved ankle brace of claim 13, wherein the recessed area is configured to collapse in conjunction with extension of the foot.

15. The improved ankle brace of claim 12, wherein the material strip is disposed above a heel portion of the ankle brace.

16. The improved ankle brace of claim 12, wherein the material strip includes an upper Achilles portion and a lower heel portion, the Achilles portion having one directional stretch and the heel portion having two directional stretch.

* * * * *